(12) United States Patent  (10) Patent No.: US 6,436,060 B1
Talish  (45) Date of Patent: Aug. 20, 2002

(54) SUBMERSIBLE SYSTEM FOR ULTRASONIC TREATMENT

(75) Inventor: Roger J. Talish, Hillsborough, NJ (US)

(73) Assignee: Exogen, Inc, Piscataway, NJ (US)

( * ) Notice: Subject to any disclaimer, the term of this patent is extended or adjusted under 35 U.S.C. 154(b) by 0 days.

(21) Appl. No.: 09/420,273

(22) Filed: Oct. 18, 1999

Related U.S. Application Data

(63) Continuation of application No. PCT/US98/07549, filed on Apr. 16, 1998.
(60) Provisional application No. 60/053,933, filed on Jul. 28, 1997, and provisional application No. 60/044,711, filed on Apr. 18, 1997.

(51) Int. Cl.[7] ................................................. A61B 5/00
(52) U.S. Cl. ............................................ 601/2; 607/86
(58) Field of Search ............................ 601/2, 148, 156, 601/157, 167; 600/439; 5/601, 615, 621–624; 4/495, 496

(56) References Cited

U.S. PATENT DOCUMENTS

| | | | |
|---|---|---|---|
| 3,550,586 A | 12/1970 | Balamuth | |
| 3,961,380 A | * 6/1976 | Garr | 4/162 |
| 4,170,045 A | * 10/1979 | Estes | 4/177 |
| 4,216,766 A | 8/1980 | Duykers et al. | |
| 4,269,797 A | 5/1981 | Mikiya et al. | |
| 4,312,536 A | * 1/1982 | Lloyd | 297/217 |
| 4,446,586 A | * 5/1984 | Reed et al. | 4/555 |
| 4,530,360 A | 7/1985 | Duarte | |
| 4,630,323 A | * 12/1986 | Sage et al. | 4/580 |
| 4,891,849 A | * 1/1990 | Robinson | 4/575 |
| 5,211,160 A | 5/1993 | Talish et al. | |
| 5,339,804 A | 8/1994 | Kemp | |
| 5,380,269 A | * 1/1995 | Urso | 602/19 |
| 5,520,612 A | 5/1996 | Winder et al. | |
| 5,556,372 A | 9/1996 | Talish et al. | |
| 5,702,353 A | 12/1997 | Guzzini et al. | |
| 5,741,317 A | * 4/1998 | Ostrow | 607/85 |
| 5,743,862 A | * 4/1998 | Izumi | 601/2 |

FOREIGN PATENT DOCUMENTS

| | | |
|---|---|---|
| IT | 0695559 | 2/1996 |
| WO | WO 95/03744 | 2/1995 |
| WO | WO 97/33649 | 9/1997 |

* cited by examiner

*Primary Examiner*—Marvin M. Lateef
*Assistant Examiner*—Eleni Mantis Mercader
(74) *Attorney, Agent, or Firm*—Bruce D. Gray; Kristin L. Johnson; Kilpatrick Stockton LLP

(57) ABSTRACT

The system is used for therapeutically treating injuries using ultrasound. The system includes an ergonomically constructed ultrasonic transducer treatment head module and a main operating unit. The transducer treatment head module is positioned adjacent the area of the injury and excited for a predetermined period of time. The system includes a bathtub insert that envelops a portion of the patient's body, and means on the insert for positioning and holding the treatment head module adjacent positions on the patient's body.

20 Claims, 7 Drawing Sheets

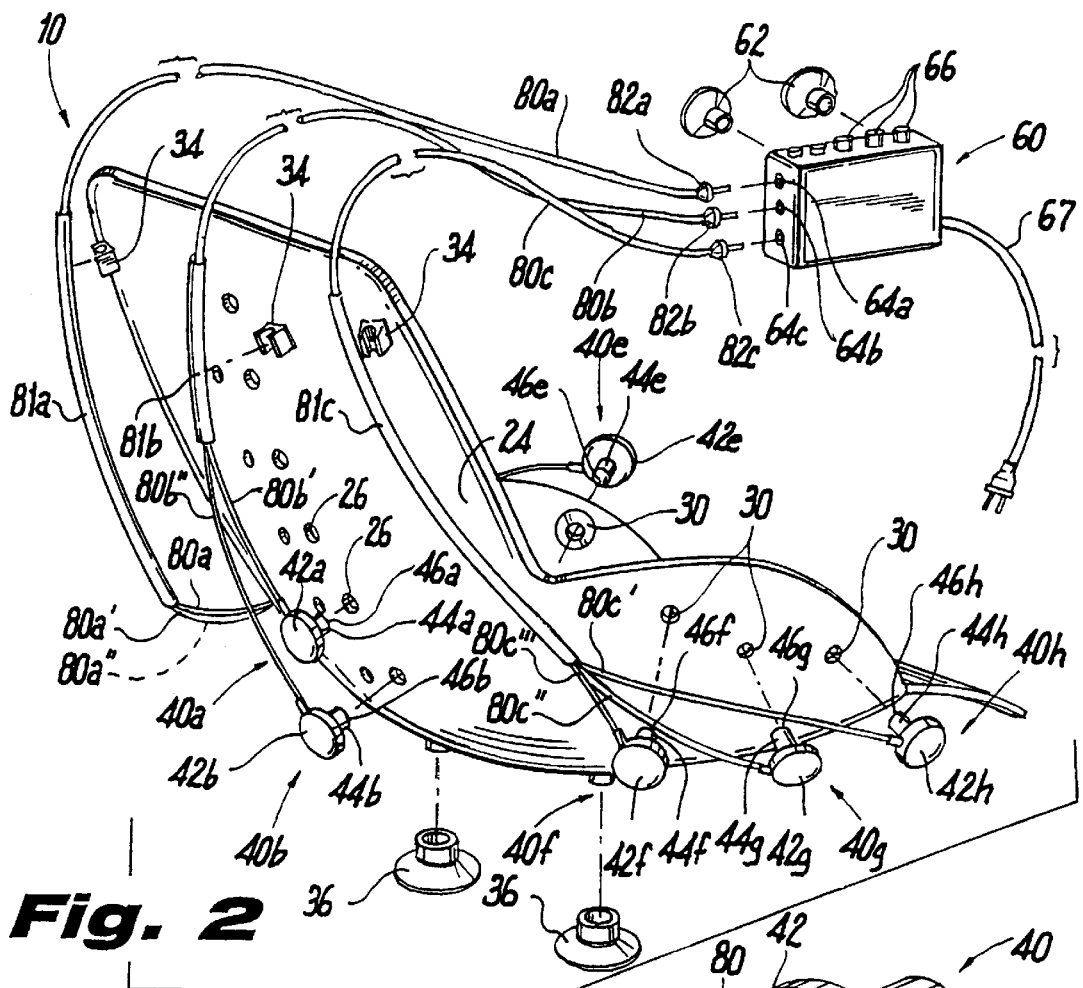
Fig. 2
Fig. 2a
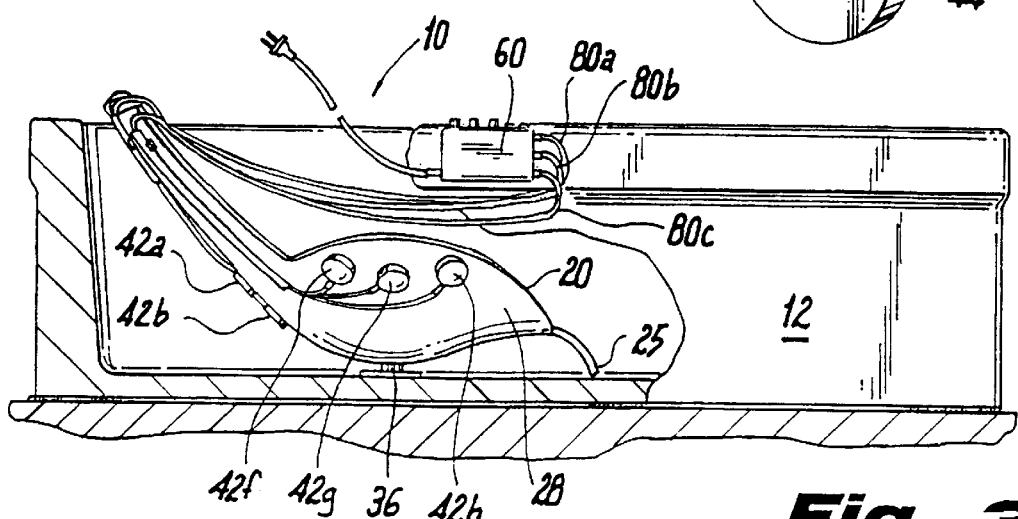
Fig. 3

SUBMERSIBLE SYSTEM FOR ULTRASONIC TREATMENT

This is a continuation continuation-in-part of application Ser. No. PCT/US98/07549 filed Apr. 16, 1998, which claims the benefit of provisional applications 60/044,771 filed on Apr. 18, 1997 qand Ser. No. 60/053,933 filed on Jul. 28, 1997.

BACKGROUND OF THE INVENTION

1. Field of the Invention

The present invention relates to a system for therapeutically treating bone structure using ultrasound. More particularly, the present invention relates to a system that includes a bathtub insert for use in treating bone injuries or a variety of musculoskeletal injuries and/or problems.

2. Description of the Related Art

The use of ultrasound to therapeutically treat and evaluate bone injuries is known. Impinging ultrasonic pulses having appropriate parameters, e.g., frequency, pulse repetition, and amplitude, for suitable periods of time and at a proper external location adjacent to a bone injury has been determined to accelerate the natural healing of, for example, bone breaks and fractures. For patients with reduced healing capacity, such as elderly persons with osteoporosis, ultrasonic therapy may promote healing of bone injuries that would otherwise require prosthetic replacement or leave the patient permanently disabled.

U.S. Pat. No. 4,530,360 to Duarte describes a basic non-invasive therapeutic technique and apparatus for applying ultrasonic pulses from a transducer surface placed on the skin at a location adjacent a bone injury. The applicator described in the '360 patent has a plastic tube which serves as a grip for the operator, an RF plug attached to the plastic tube for connection to an RF source, and internal cabling connected to an ultrasonic transducer. To apply the ultrasound pulses during treatment an operator must manually hold the applicator in place until the treatment is complete. As a result, the patient is, in effect, immobilized during treatment. The longer the treatment period, the more the patient and/or the assistant is inconvenienced, and certain parts of the body, such as the back, cannot be reached by the patient with such a device, thus requiring the help of an assistant. The '360 patent also describes a range of RF signals for creating the ultrasound, ultrasound power density levels, a range of duration for each ultrasonic pulse, and a range of ultrasonic pulse frequencies.

In general, an ultrasound carrier frequency between 250 kHz and 10 MHz coupled with a relatively low-frequency modulating signal (e.g. 5 Hz to 10 kHz) and low intensity acoustic signal (e.g. less than 100 milliwatts/cm$^2$) aids, and will be effective for therapeutic treatment.

U.S. Pat. No. 5,211,160 to Talish et al. relates to an ultrasonic treatment system with a mounting fixture that attaches to a patient's limb using straps and a hook and loop attachment. The body application unit interfaces with the mounting fixture so that the operative surface is adjacent the skin location.

While the systems described in these patents relate to therapeutic methods and apparatus for ultrasonically treating injured bone, and describe basic mounting fixtures for use with a cast or limb for attaching the body applicator unit to the patient, they do not disclose therapeutic ultrasonic delivery systems having a device that permits placement of one or more transducers adjacent various parts of the body that are either hard-to-reach or, because of the topology of the external skin location, make it difficult to manually position and maintain a transducer adjacent thereto.

Therefore, a need exists for an apparatus which permits placement of one or more body-applicator units adjacent various parts of the body that are hard-to-reach or otherwise hard to manually position or maintain a transducer adjacent thereto.

SUMMARY OF THE INVENTION

The ultrasonic treatment apparatus of the present invention is used for preventing osteopenia, promoting bone and soft tissue growth, ingrowth, and healing of bone and soft tissue. The apparatus includes a main operating unit, including a signal generator for providing excitation signals for an ultrasonic transducer head module. At least one submergible ultrasonic treatment head module is also provided including a receiving component and an ultrasonic generation component for providing ultrasonic waves from an exposed operative surface positionable adjacent a skin location. The receiving component receives the excitation signals from the signal generator and provides input signals to the ultrasonic generation component for the generation of ultrasonic waves at the operative surface. An interface between the main operating unit and the receiving component of the ultrasonic treatment head module transmits the excitation signals from the signal generator to the receiving component. A housing configured (or configurable) at least in part to contour to a region of a human body includes at least one receptacle for holding the at least one ultrasonic treatment head module with the transducer surface adjacent a skin location when the housing is positioned adjacent the region of the human body.

The housing of the present invention encompasses an insert that is suitable for submersion in a tub, including a variety of specific configurations adapted for treatment on various regions of the torso that are prone to osteopenia or injury, such as the hip and the spine. (For the purposes of this application, the spine is defined to extend from the cervical vertebrae to the coccyx.) In its most generic embodiment, the insert is a seat-like mold that extends from the back of the thighs to the upper back, and around the hips of the user. The insert is also configured to be received within a standard residential bathtub. The insert provides for adjusting the position of the transducer surface of the ultrasonic treatment module so that it interfaces with the external skin location corresponding to the injury targeted for treatment.

The ultrasonic delivery system for therapeutic use of the present invention also includes at least one ultrasonic treatment module with a telescoping portion, the distal end of the telescoping portion defining a forward planar region. An ultrasonic generation means is housed within the at least one ultrasonic treatment module and includes an exposed transducer surface substantially parallel with the forward planar region of the telescoping portion. The system further includes a positionable insert contoured to a portion of a human body, the insert having at least one receptacle for retaining and aligning the at least one ultrasonic treatment module with the transducer surface adjacent the human body when the insert is positioned adjacent the portion of the human body it is contoured to.

BRIEF DESCRIPTION OF THE DRAWINGS

Preferred embodiments of the invention are described below with reference to the drawings, which are described as follows:

FIG. 2 is an side/rear exploded perspective view of the ultrasonic delivery system of FIG. 1;

FIG. 2a is a perspective view of an ultrasonic treatment head module of the ultrasonic delivery system of FIG. 1;

FIG. 3 is a partially cut-away side view of the ultrasonic delivery system of FIG. 1 inserted in a bathtub;

DETAILED DES ON OF THE PREFERRED EMBODIMENTS

Figure 1:
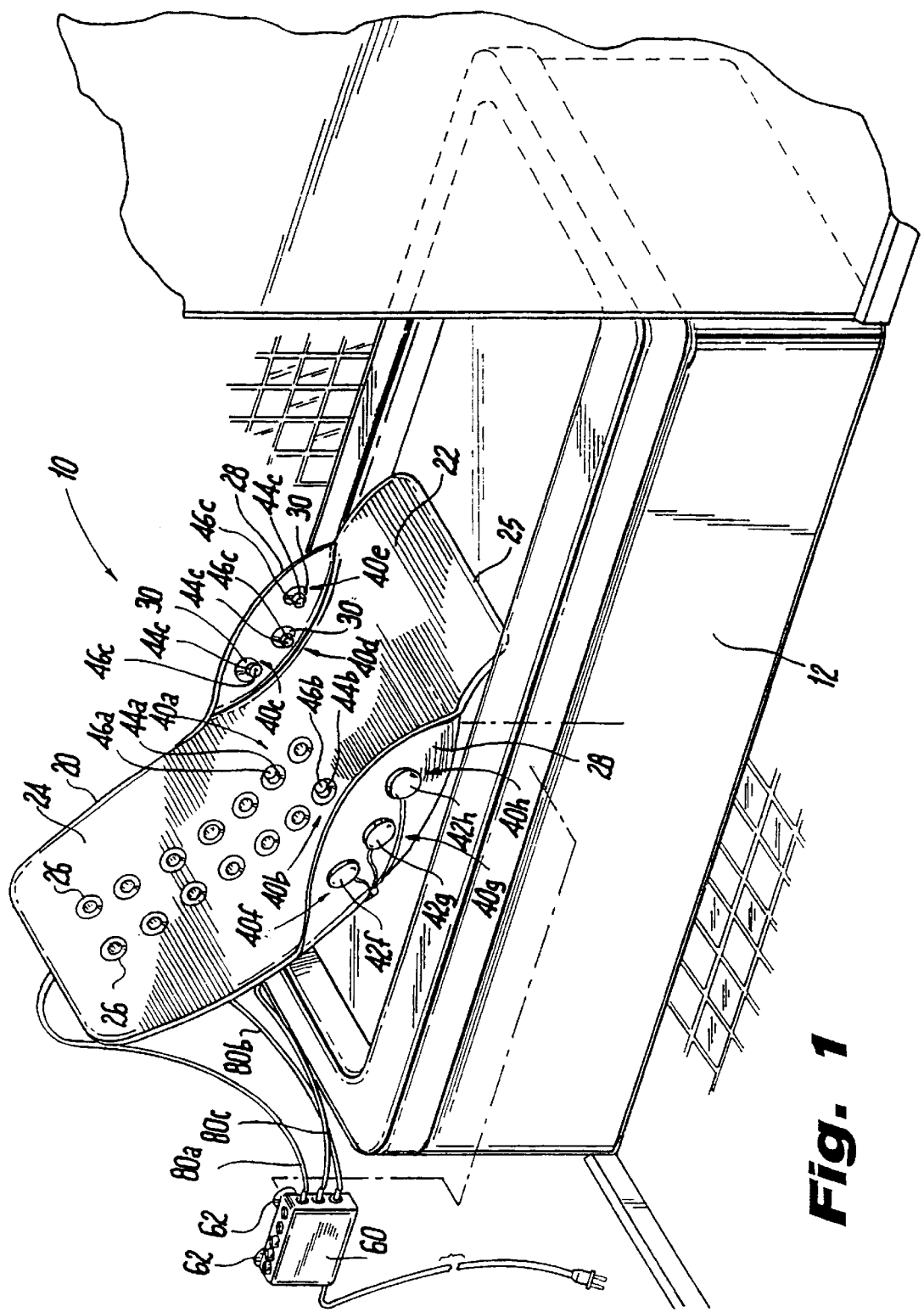
FIG. 1 is an exploded, perspective view of an ultrasonic delivery system according to the present invention, including apparatus for creating the therapeutic ultrasound and an insert that is suitable for submersion in a tub for positioning the transducer surface(s) of the ultrasonic delivery system.

The ultrasonic treatment apparatus of the present invention is used for therapeutically treating injuries using ultrasound and for preventing osteopenia, promoting bone and soft tissue growth, ingrowth and healing of bone and soft tissue. Although shown here for the treatment of musculoskeletal injuries, other injuries including venous ulcers are also contemplated. The apparatus includes an ergonomically constructed ultrasonic transducer assembly. The ultrasonic transducer assembly is constructed so that it is submergible without danger of electric shock to a patient. The apparatus also utilizes a main operating unit (MOU) which provides control signals for the ultrasonic transducer treatment head module. The apparatus also includes an insert that is suitable for submersion in a tub and configured (or configurable) to contour at least in part to, and thus receive, a region of a human body. The insert includes receptacles adapted for holding at least one ultrasonic treatment head module with the operative surface adjacent a skin location of the torso region when the torso region is received in the insert. In operation, the transducer treatment head module is positioned adjacent the injured area and excited for a predetermined period of time, thus delivering therapeutic ultrasonic treatment to the particular region of the torso while the patient is in the tub.

The MOU and ultrasonic treatment head module, including the electronics and components of the device, are further described in commonly-owned U.S. patent application Ser. Nos. 08/389,148 and 08/367,471, which are incorporated by reference into this application. In general, the MOU and ultrasonic treatment head modules of those applications are adaptable to the system of the present invention. Those particular aspects of the MOU and ultrasonic treatment head modules that are preferably modified from the descriptions in those applications will be described below. For example, the transducer head modules and a portion of the interface with the MOU in the present invention must be submersible, which is not portrayed in the above-referenced applications. Also, for example, it is not necessary to utilize the portable, ergonomically constructed design of the MOU of the above-referenced applications in the present invention. The system of the present invention contemplates a stationary patient immersed in a bathtub, where the mobility of the MOU is less important. The components and electronics of the MOU and ultrasonic treatment head modules of the above-referenced applications, however, may be incorporated directly into the systems of the present invention.

Also, although the above-referenced applications show a single transducer treatment head module, the present invention envisions a plurality of modules for use with a single MOU. (Construction of an MOU to house the electronics necessary to service a plurality of ultrasonic head treatment modules would be a routine task for one skilled in the art using the descriptions for a single module in the above-referenced applications.) The plurality of modules, for example, may all be activated at once.

FIG. 1 shows an exploded, perspective view of a preferred embodiment of the system 10 for delivering ultrasonic therapeutic treatment to the spine and lower back, a region of the torso where it is difficult to position and maintain an ultrasonic treatment module, as well as the hips. Prominently included in the system 10 of FIG. 1 is a bathtub insert 20 that is received in a bathtub 12 of the size found in most homes. (The nominal dimensions of such a bathtub are approximately 5'×2.5'×2'.) The bathtub insert 20 shown is roughly in the shape of a reclining seat, with a bottom portion 22 that rests on the bottom surface of the bathtub 12 when inserted therein. Extending the length of the back portion 24 of insert 20 are two columns of back receptacles 26 that pass through insert 20. Extending through the side portions 28 are hip receptacles 30. The back and hip receptacles 26, 30 are configured to receive and retain the therapeutic ultrasonic treatment head modules 40a–h, as described in more detail below.

A main operating unit ("MOU") 60 is shown that attaches to the side of the tub 12. Cables 80a–c extend from MOU 60 to treatment head modules 40a–h, as described further below.

FIG. 2 is a side/rear exploded perspective view of the system of FIG. 1. As noted, insert 24 has a reclining seat-like shape with back receptacles 26 and hip receptacles 30. As seen in from the front view of the receptacles (also seen in FIG. 1), the passages through the insert that create the back and hip receptacles 26, 30 have rubber grommets 26', 30' that serve to secure the ultrasonic treatment head modules 40a–h in position for treatment, as described further below. Insert 20 is supported in an upright position at the bottom of the tub 12 by a set of rubber suction cups 36 and the front lip 25 of the insert 20, as shown in FIG. 3.

As also noted above, ultrasonic treatment head modules 40a–h are received in back receptacles 26 and hip receptacles 30. FIG. 2a shows an ultrasonic treatment head module 40 representing each ultrasonic treatment head module 40a–h. (Like features of the ultrasonic treatment head modules 40*a–h* depicted in the other figures will be referenced with the same numbers and a corresponding suffix.) Module 40 includes a forward projecting portion 44 and a flange portion 42 adjacent one end of projecting portion 44. The flange portion 44 is opposite the transducer surface 46. Interface cable 80 extends into the treatment head module 40 through the rim of flange portion 42.

The ultrasonic treatment module 40 should be waterproof, so that its internal electronic components are protected when it is submerged, as contemplated by the system of the present invention. Waterproof seals, jacks and plugs that may serve this purpose are well known. (As described below, a portion of the interface cable 80 is also received in the bathtub and should thus be waterproof, and the junction between the cable 80 and flange portion 42 should also be waterproof. Ways of providing such waterproof seals are likewise well known.) The waterproofing will also serve to protect the patient from an electric shock from the ultrasonic treatment head module, although the power required by the ultrasonic treatment head module (to power the components and the transducer) is adequately supplied by a lithium battery, and would not pose a risk of harmful electric shock to a patient.

Referring back to FIG. 2, the forward projecting portions 44*a–h* extend through one of the back receptacles 26 or hip receptacles 30 of insert 24. (Only projecting portions 44*a–e* of ultrasonic treatment head modules 40*a–e* are visible in FIG. 1.) Grommets 26', 30' frictionally engage the forward projecting portions of the modules 40*a–h*, thus holding and positioning the modules 40*a–h* so that the transducer surfaces 46*a–h* project out of the front surface of the insert 24. (Only transducer surfaces 46*a–e* of modules 40*a–e* are visible in FIG. 1.) The "front surface" of insert 24 is defined as that side of the insert that receives and envelops the patient. The flange portions 42*a–h* of ultrasonic treatment modules 40*a–h* prevent the ultrasonic treatment head modules 40*a–h* from passing through the back or hip receptacles 26, 30. (Only flange portions 42*f–h* of modules 40*f–h* are visible in FIG. 1.) MOU 60 includes a pair of suction cups 62 that allow mounting of MOU 60 on the outside of the bathtub 12. (See FIGS. 1 and 3.) Jacks 64*a–c* receive plugs 82*a–c* of interface cables 80*a–c*. MOU 60 may be programmed for the therapy of a particular patient by control settings 66, which may include an interface for data from an external computer and/or a visual display. MOU 60 is powered via electric plug 68.

Interface cables 80*a–c* extend between MOU 60 and the ultrasonic treatment head modules 40*a–h*, thus providing the path for the driving signals created by the MOU 60 to the modules 40*a–h*. As shown in FIG. 2, interface cables 80*a–c* may be split so that each cable provides driving signals to a number of ultrasonic treatment head modules. For example, in FIG. 2, interface cable 80*b* is split into two cables 80*b*', 80*b*", which provide driving signals to treatment head modules 40*a*, 40*b*, respectively. Similarly, interface cable 80*a* is depicted split into three cables 80*a*', 80*a*", 80*a*''', providing signals to ultrasonic treatment head modules 40*c*, 40*d*, 40*e*, and interface cable 80*c* is depicted split into three cables 80*c*', 80*c*", 80*c*''', providing signals to ultrasonic treatment head modules 40*f*, 40*g*, 40*h*. (See FIG. 1 in conjunction with FIG. 2.) The interface cables 80*a–c* (and their branch cables 80*a*', 80*a*", 80*a*'''; 80*b*', 80*b*'; and 80*c*', 80*c*", 80*c*''', respectively) are partially surrounded by tubing 81*a*, 81*b*, 81*c*, respectively, which is held adjacent the back surface of insert 24 by three clamps 34.

Figure 4:
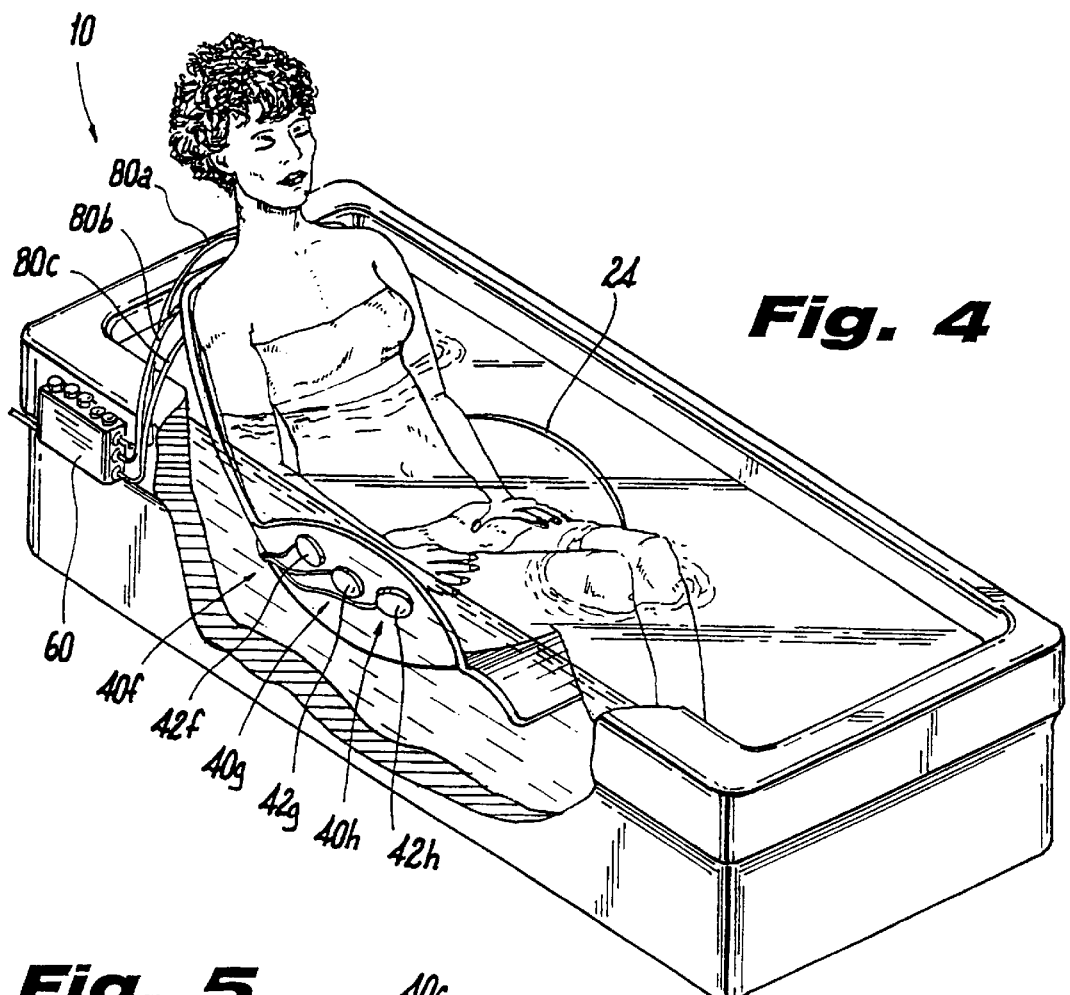
FIG. 4 is a perspective partially cut-away view of the ultrasonic delivery system of FIG. 1 being used by a patient during treatment.

FIG. 4 shows the system 10 of the present invention delivering therapeutic ultrasound to a patient enveloped in the insert 24. As noted above, the projecting portions 44*a–h* of ultrasonic treatment head modules 40*a–h* position their transducer surfaces 46*a–h* so that they project out of the interior surface of the insert 24 (see FIG. 1) and the transducer surfaces 46*a–h* engage the skin when the patient sits in the insert 24. The MOU 20 provides driving signals over the interface cables 80*a–c* (and their branches 80*a*', 80*a*", 80*a*''', 80*b*', 80*b*", 80*c*', 80*c*", 80*c*''') to the ultrasonic transducer treatment head modules 40*a–h*, thus creating therapeutic ultrasound at the transducer surfaces 46*a–h* (not visible in FIG. 4, but see FIGS. 1–2*a*). Referring to FIGS. 1 and 4, the ultrasonic transducer treatment head modules 40*a–h* are positioned in back and side receptacles 26, 30 so that the transducer surfaces 46*a–h* engage the external skin site of the patient where the therapeutic ultrasound is to be delivered. The water in the bathtub provides a coupling fluid between the transducer surfaces 46*a–h* and the external skin locations.

Figure 5:
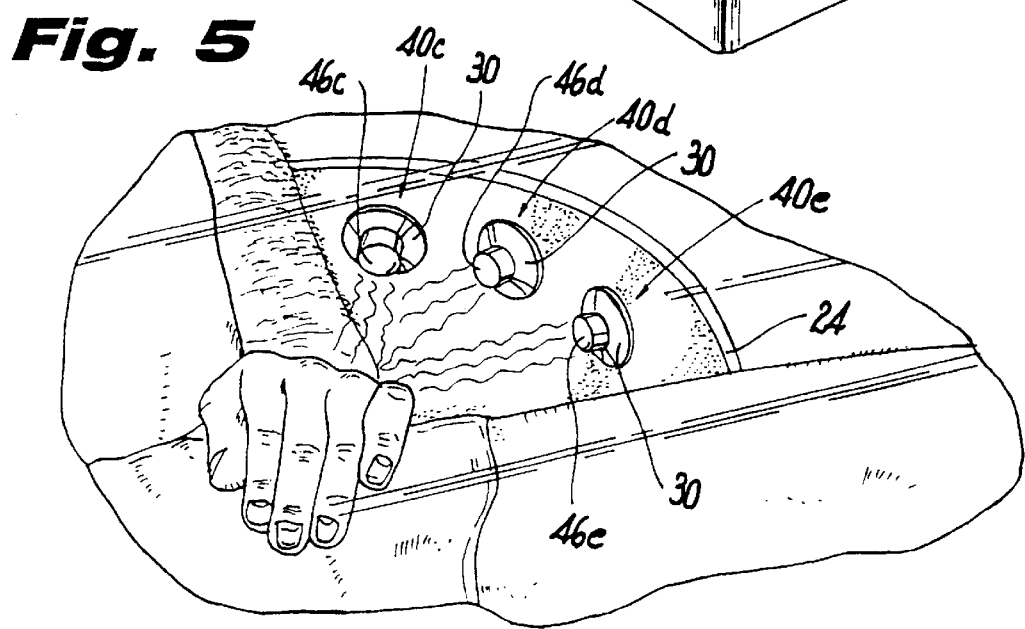
FIG. 5 is a close-up view of a portion of the system of FIG. 1 modified to provide therapeutic ultrasonic treatment to the wrist and hand area of the patient.

FIG. 5 focuses on the side portions 28 of insert 24. The side receptacles 30 of FIG. 5 have been repositioned higher than those in FIGS. 14, so that they are above the patient's hips. As shown, ultrasonic treatment head modules 40*c–e* may thus be used to deliver therapeutic ultrasound to the wrists and hands of the patient.

Figure 6:
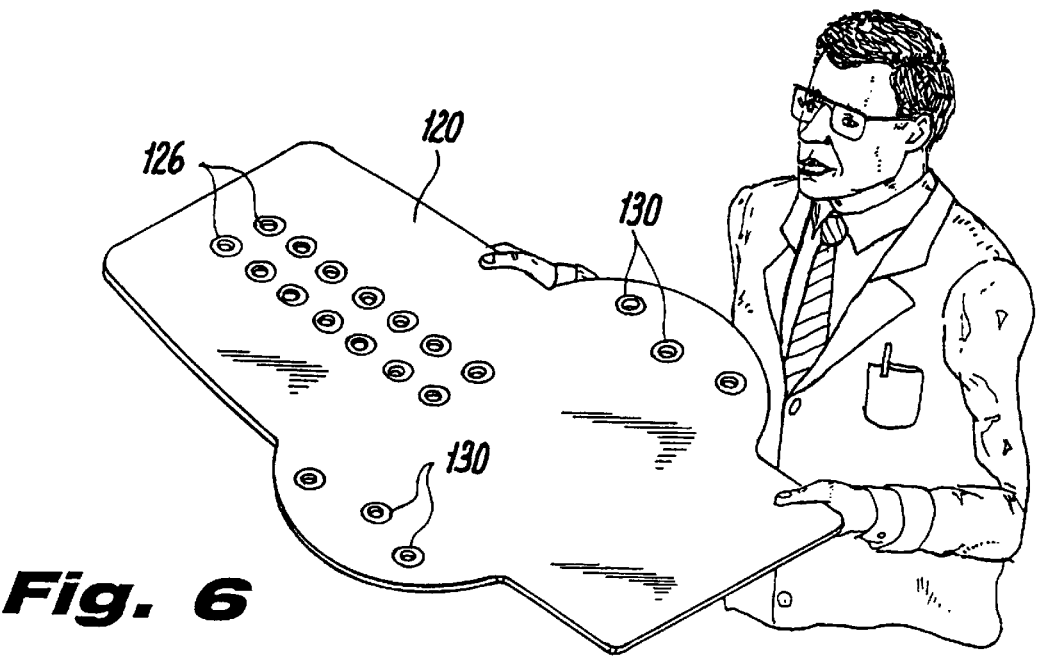
FIG. 6 is a perspective view of a flat, pre-formed insert of the present invention made of a moldable material that is heat activated.
Figure 7:
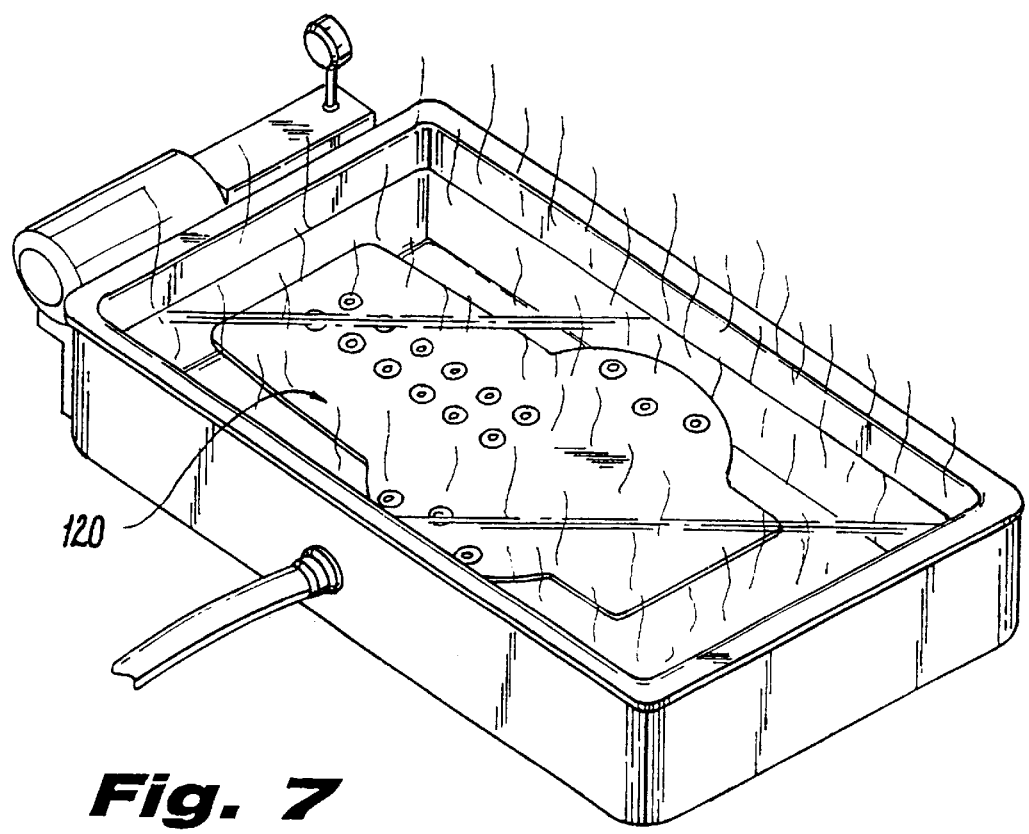
FIG. 7 is a perspective view of the insert of FIG. 6 being activated in warm bath water.
Figure 8:
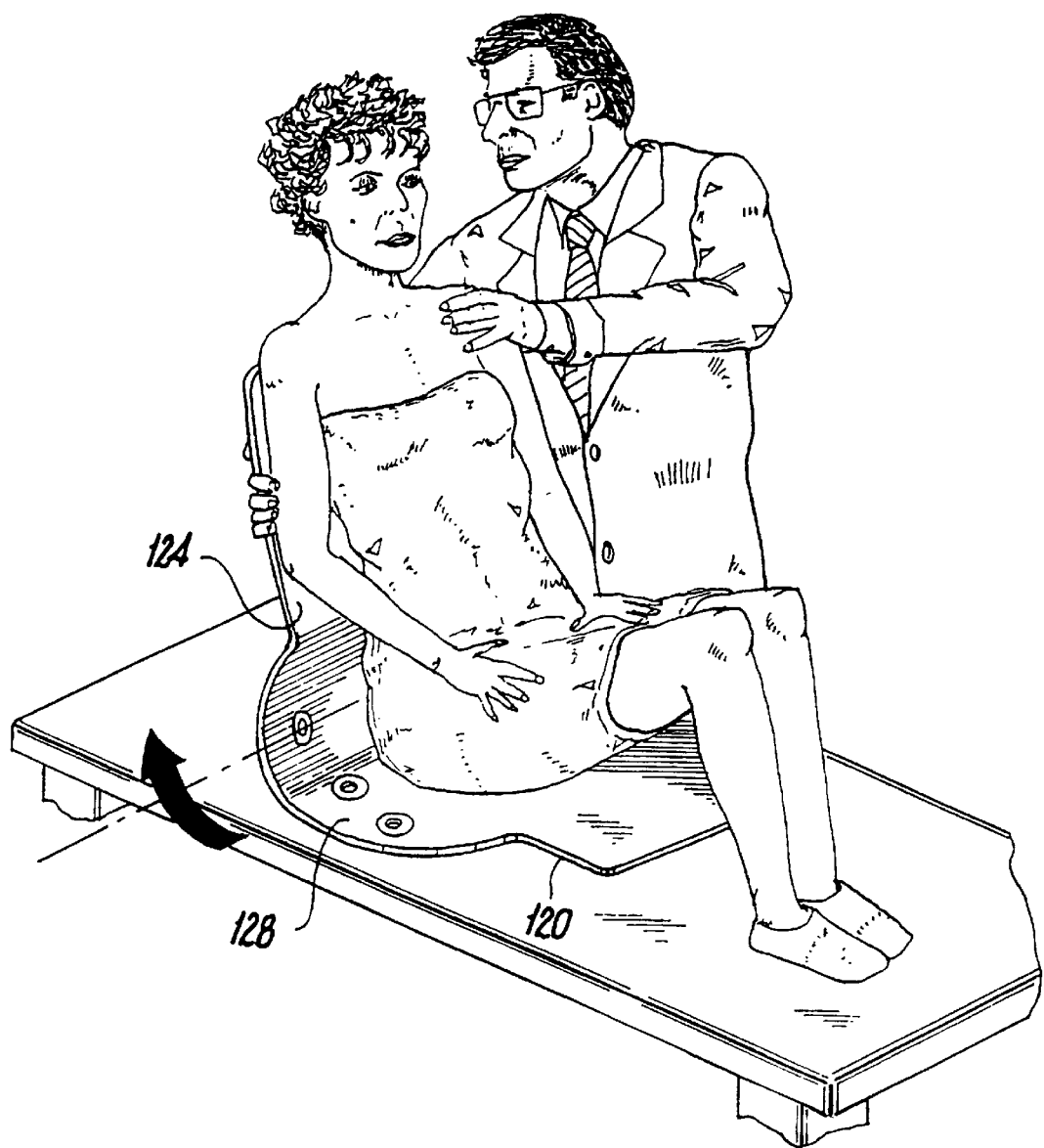
FIG. 8 is a perspective view of the activated insert of FIG. 6 being contoured to the body of a patient.
Figure 9:
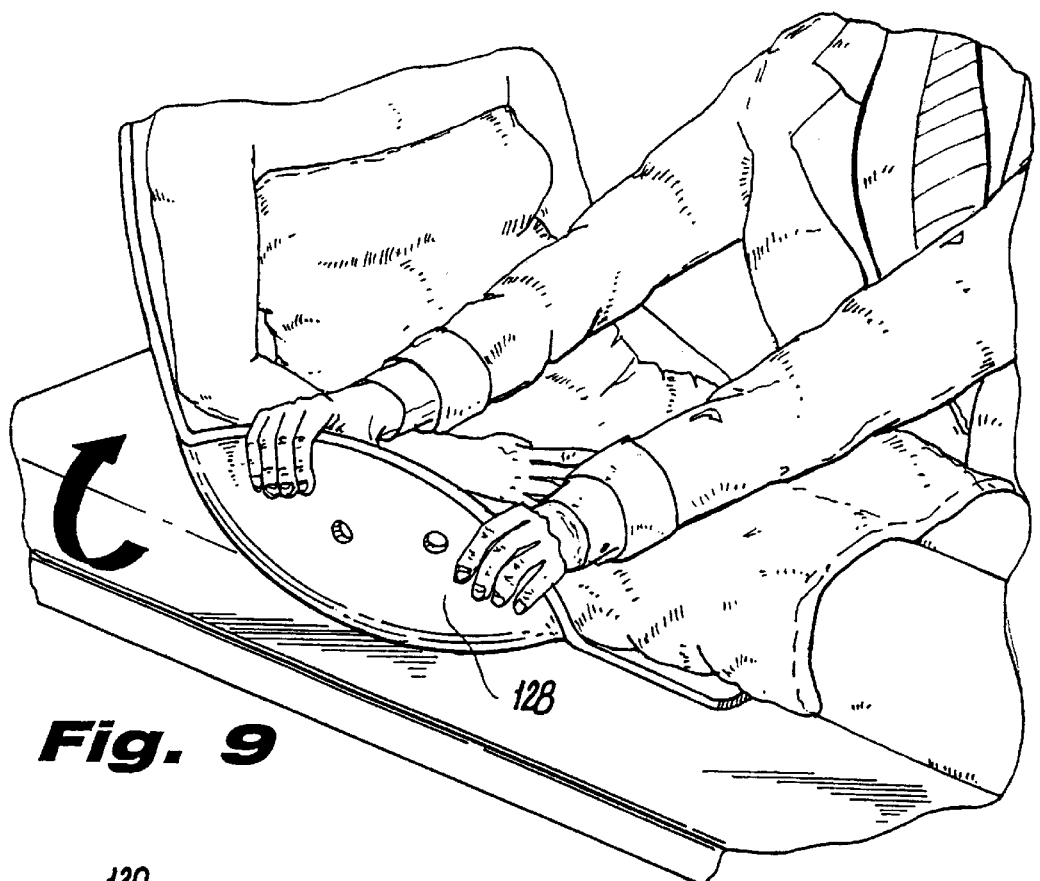
FIG. 9 is a perspective view of the activated insert of FIG. 6 being contoured to the body of a patient.
Figure 10:
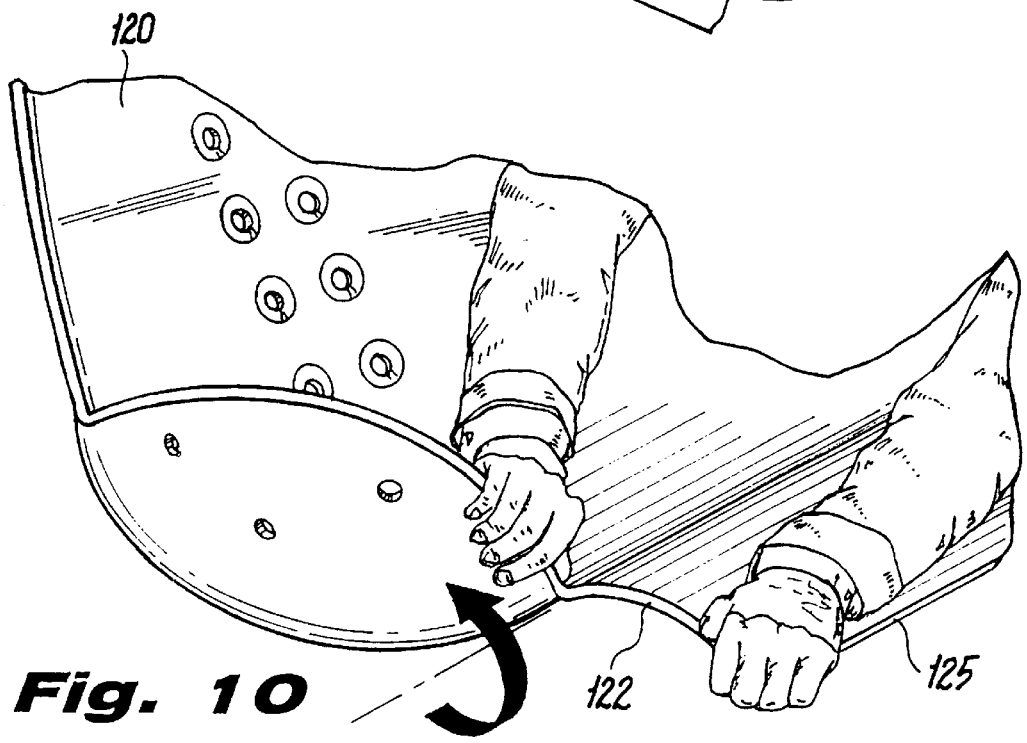
FIG. 10 is a perspective view of the activated insert of FIG. 6 being contoured to the body of a patient.

FIGS. 6–10 depict a customizable insert 120 of the present invention. The insert 120 is manufactured flat, as shown in FIG. 6, of a heat activated, moldable material, such as foam or plastics. The insert 120 is manufactured with back and side receptacles 126, 130. As shown ii FIG. 7, the moldable material of the insert 120 is activated by submerging it in warm water for the requisite period of time. As shown in FIGS. 8 and 9, while the material of the insert 120 is still warm, and thus moldable, back and hip portions 124, 128 are contoured to the back and hips of the patient. Finally, FIG. 10 shows the technician or physician putting an arc in the bottom portion 122 of insert 120, thus creating lip 125 upon which insert 120 is partially supported when inserted in a tub. (See analogous lip 25 of the insert 20 shown in FIG. 3.)

When the insert 120 as molded cools, it is closely contoured to the shape of the patient's body, allowing the transducer surfaces of the ultrasonic treatment head modules to be positioned closely to the patient's skin at the site where treatment is desired, as described below with respect to FIGS. 11 and 12.

Figure 11:
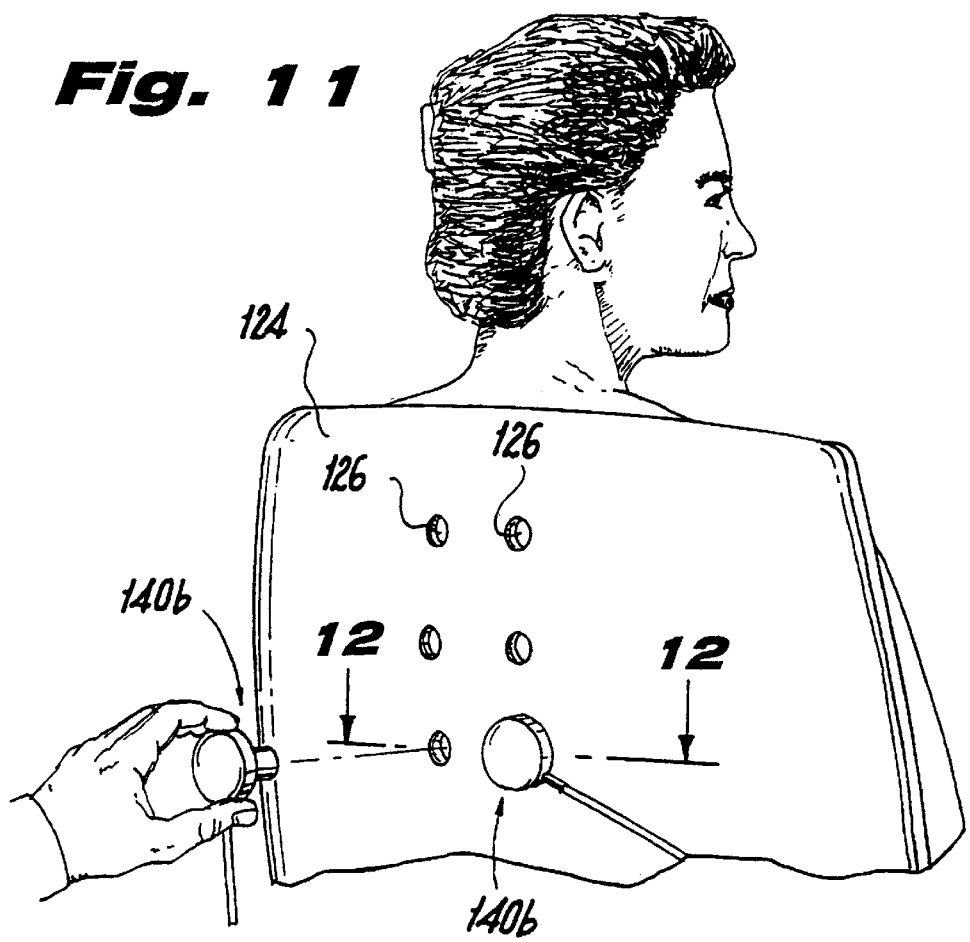
FIG. 11 is perspective view of the transducer head modules of the ultrasonic delivery system of the present invention being positioned in receiving passages in the back of the insert so that the operative surface of the transducer is adjacent the spine of the patient.
Figure 12:
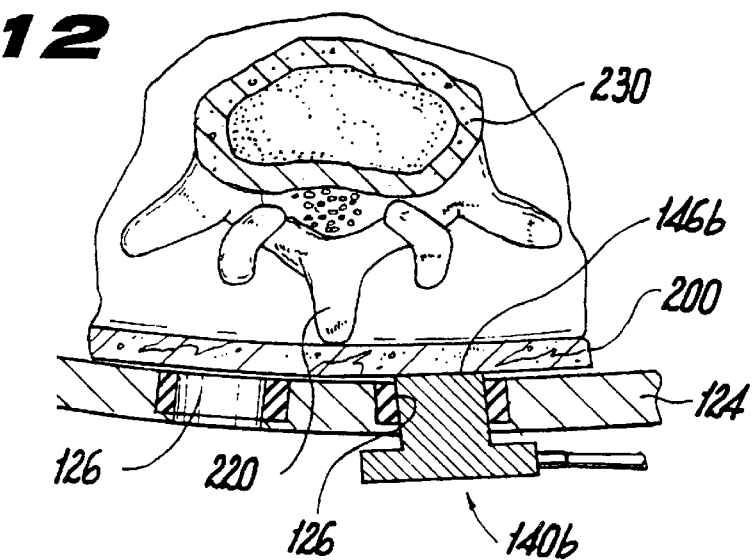
FIG. 12 is a cross-section of FIG. 11 along lines 12—12, showing the relative position of the positioned transducer head module with respect to the patient's spine.

FIG. 11 shows the technician or physician positioning the ultrasonic treatment head modules 140*a*, 140*b* in the back receptacles 126 of insert 120. FIG. 12 (a cross-section of FIG. 11 taken across lines 12—12) shows the transducer surface 146*b* of ultrasonic treatment head module 140*b* engaging the patient's skin 200 through a back receptacle 126 of insert 124. Also shown in FIG. 12 is the relative position of the patient's spine 210. Referring to FIGS. 11 and 12, the dual columns of back receptacles 126 allows the transducers to be positioned to the sides of the spinous process 220, so that the ultrasound may be directed toward the vertebral body 230.

It will be understood that various modifications can be made to the various embodiments of the present invention herein disclosed without departing from its spirit and scope. For example, the bathtub insert described above for the preferred embodiments may be replaced with a bathtub or other housing with a built-in portion that is configured at least in part to a region of the human body when received in the tub. Also, various shapes of the insert are contemplated, as well as various types of construction materials. Therefore the above description should not be construed as limiting the invention but merely as presenting preferred embodiments of the invention. Those skilled in the art will envision other modifications within the scope and spirit of the present invention as defined by the claims presented below.

What is claimed is:

1. An ultrasonic delivery system for therapeutic use comprising:
   a main operating unit, including a signal generator for providing excitation signals for at least one ultrasonic treatment head module;
   at least one waterproof, submergible ultrasonic treatment head module comprising a receiving component and an ultrasonic generation component for providing ultrasonic waves from an exposed operative surface positionable adjacent a skin location, the receiving component receiving the excitation signals from the signal generator and providing input signals to the ultrasonic generation component, whereby the ultrasonic generation component generates ultrasonic waves at the operative surface thereof in response to the input signals, and wherein internal electronic components of the treatment head module are protected from exposure to water when submerged;
   an interface between the main operating unit and the receiving component of the ultrasonic treatment head module for transmitting the excitation signals from the signal generator to the receiving component; and
   a housing configured at least in part to contour to a region of a human body, the housing including at least one receptacle for holding the at least one ultrasonic treatment head module with the operative surface adjacent a skin location when the housing is positioned adjacent the region of the human body.

2. The ultrasonic delivery system as in claim 1, wherein the housing is configured at least in part to contour to the region of the human body corresponding to at least a portion of the spine.

3. The ultrasonic delivery system as in claim 1, wherein the at least one ultrasonic treatment head module includes a projecting portion housing the operative surface.

4. The ultrasonic delivery system as in claim 3, wherein the at least one receptacle of the housing comprises a passage through the housing that receives the projecting portion of the at least one ultrasonic treatment head module, such that the operative surface of the at least one treatment head module protrudes through the housing and is positioned adjacent a skin location when the housing is positioned adjacent the region of the human body to which it is contoured.

5. The ultrasonic delivery system as in claim 1, wherein the housing is an insert that may be received in a bathtub, the insert configured at least in part to contour to the external region of a human body corresponding to the hip.

6. The ultrasonic delivery system as in claim 1, wherein the housing is an insert that may be received in a bathtub, the insert in the shape of a recumbent seat such that it is configured at least in part to contour to the back, buttocks and hip regions of a human body.

7. The ultrasonic delivery system as in claim 6, wherein the insert comprises at least one receptacle, each receptacle comprising a passage through the insert.

8. The ultrasonic delivery system as in claim 7, wherein at least one of the passages extends through the insert approximately where the insert is configured to contour to the external region of the body.

9. The ultrasonic delivery system as in claim 8, wherein the external region of the body corresponds to the spine.

10. The ultrasonic delivery system as in claim 8, wherein the external region of the body corresponds to the hips.

11. The ultrasonic delivery system as in claim 1, wherein the housing is an insert having sufficient dimensions that the insert will fit in a standard residential bathtub.

12. The ultrasonic delivery system as in claim 1, wherein at least a portion of the interface between the main operating unit and the receiving component of the ultrasonic treatment head module is waterproof.

13. The ultrasonic delivery system as in claim 1, wherein the housing comprises a tub that receives a human body.

14. The ultrasonic delivery system as in claim 13, wherein the tub is configured at least in part to contour to the back and hips of the human body when the human body is received in the tub.

15. An ultrasonic delivery system for therapeutic use comprising:
   a main operating unit, including a signal generator for providing excitation signals for at least one ultrasonic treatment head module;
   at least one waterproof, submergible ultrasonic treatment head module comprising a receiving component and an ultrasonic generation component for providing ultrasonic waves from an exposed operative surface positionable adjacent a skin location, the receiving component receiving the excitation signals from the signal generator and providing input signals to the ultrasonic generation component, whereby the ultrasonic generation component generates ultrasonic waves at the operative surface thereof in response to the input signals, and wherein internal electronic components of the treatment head module are protected from exposure to water when submerged;
   an interface between the main operating unit and the receiving component of the ultrasonic treatment head module for transmitting the excitation signals from the signal generator to the receiving component; and
   an insert that may be received in a bathtub and configured at least in part to contour to an external region of a body, wherein the insert includes at least one receptacle for holding the at least one ultrasonic treatment head module with the operative surface adjacent a skin location when the insert is positioned adjacent the region of the body.

16. The ultrasonic delivery system as in claim 15, wherein the at least one receptacle comprises a passage through the insert.

17. The ultrasonic delivery system as in claim 16, wherein the passage extends through the insert approximately where the insert is configured to contour to the external region of the body.

18. The ultrasonic delivery system as in claim 17, wherein the external region of the body corresponds to the spine.

19. The ultrasonic delivery system as in claim 17, wherein the external region of the body corresponds to the hips.

20. A method of delivering ultrasound to a patient comprising:
   providing an ultrasonic delivery system comprising:
      a main operating unit, including a signal generator for providing excitation signals for at least one ultrasonic treatment head module,
      at least one waterproof, submergible ultrasonic treatment head module comprising a receiving component and an ultrasonic generation component for providing ultrasonic waves from an exposed operative surface positionable adjacent a skin location of a patient, the receiving component receiving the excitation signals from the signal generator and providing input signals to the ultrasonic generation component, whereby the ultrasonic generation component generates ultrasonic waves at the operative surface thereof in response to the input signals, and wherein internal electronic components of the treatment head module are protected from exposure to water when submerged;

an interface between the main operating unit and the receiving component of the ultrasonic treatment head module for transmitting the excitation signals from the signal generator to the receiving component; and a housing configured at least in part to contour to a region of the patient's body, the housing including at least one receptacle for holding the at least one ultrasonic treatment head module with the operative surface adjacent a skin location when the housing is positioned adjacent the region of the patient's body;

positioning the housing adjacent the region of the patient's body; and generating ultrasound to promote healing in the region of the patient's body.

* * * * *